United States Patent [19]

Perzan et al.

[11] Patent Number: 5,419,435
[45] Date of Patent: May 30, 1995

[54] SHARPS DISPOSAL SYSTEM INCLUDING REUSABLE CONTAINER

[75] Inventors: Ugo P. Perzan, Fort Lauderdale; Joe D. Hutto, Ft. Myers; Richard Blanchette, Ft. Myers Beach, all of Fla.

[73] Assignee: Medx, Inc., Miami, Fla.
[21] Appl. No.: 255,598
[22] Filed: Jun. 8, 1994
[51] Int. Cl.[6] .................... B65D 83/10; B65D 83/02
[52] U.S. Cl. .................. 206/366; 206/63.5; 206/438; 220/481; 220/210; 70/345; 292/80; 292/87; 292/91; 292/DIG. 38
[58] Field of Search ............... 206/366, 63.5, 438; 220/481, 210; 70/345; 292/80, 87, 91, D38

[56] References Cited

U.S. PATENT DOCUMENTS

| | | | |
|---|---|---|---|
| 1,121,388 | 12/1914 | Milks | 220/481 |
| 4,453,648 | 6/1984 | Harris et al. | |
| 4,702,385 | 10/1987 | Shillington et al. | |
| 4,715,498 | 12/1987 | Hanifl | |
| 4,736,860 | 4/1988 | Bemis | |
| 4,809,850 | 3/1989 | Laible et al. | |
| 4,828,107 | 5/1989 | Spencer | 206/366 |
| 4,877,150 | 10/1989 | Otto et al. | 206/366 |
| 4,955,477 | 9/1990 | Bruno | |
| 5,046,613 | 9/1991 | Baudry et al. | |
| 5,076,429 | 12/1991 | Patrick et al. | |
| 5,103,997 | 4/1992 | Shillington et al. | |
| 5,107,990 | 4/1992 | Wicherski et al. | 206/366 |
| 5,184,721 | 2/1993 | Wengyn et al. | |
| 5,240,108 | 8/1993 | Tonna | 206/366 |
| 5,277,312 | 1/1994 | Vumbaca | |
| 5,322,164 | 6/1994 | Ricardson et al. | 206/366 |

*Primary Examiner*—Paul T. Sewell
*Assistant Examiner*—Tara L. Laster
*Attorney, Agent, or Firm*—Lott & Friedland

[57] ABSTRACT

A sharps disposal system providing a frame and a container having an opening and being selectively mountable to the frame. A lid is pivotally attached to the frame and is selectively movable into engagement with the container when the container is mounted to the frame. Engaging the container with the lid closes the opening except for an aperture through which sharps can be inserted into the container but which impedes insertion of human hands. Engaging the container with the lid also impedes removal of the container from the frame. The system employs a means for selectively locking the lid into engagement with the container. The system further provides a cover for selectively sealing said opening.

26 Claims, 3 Drawing Sheets

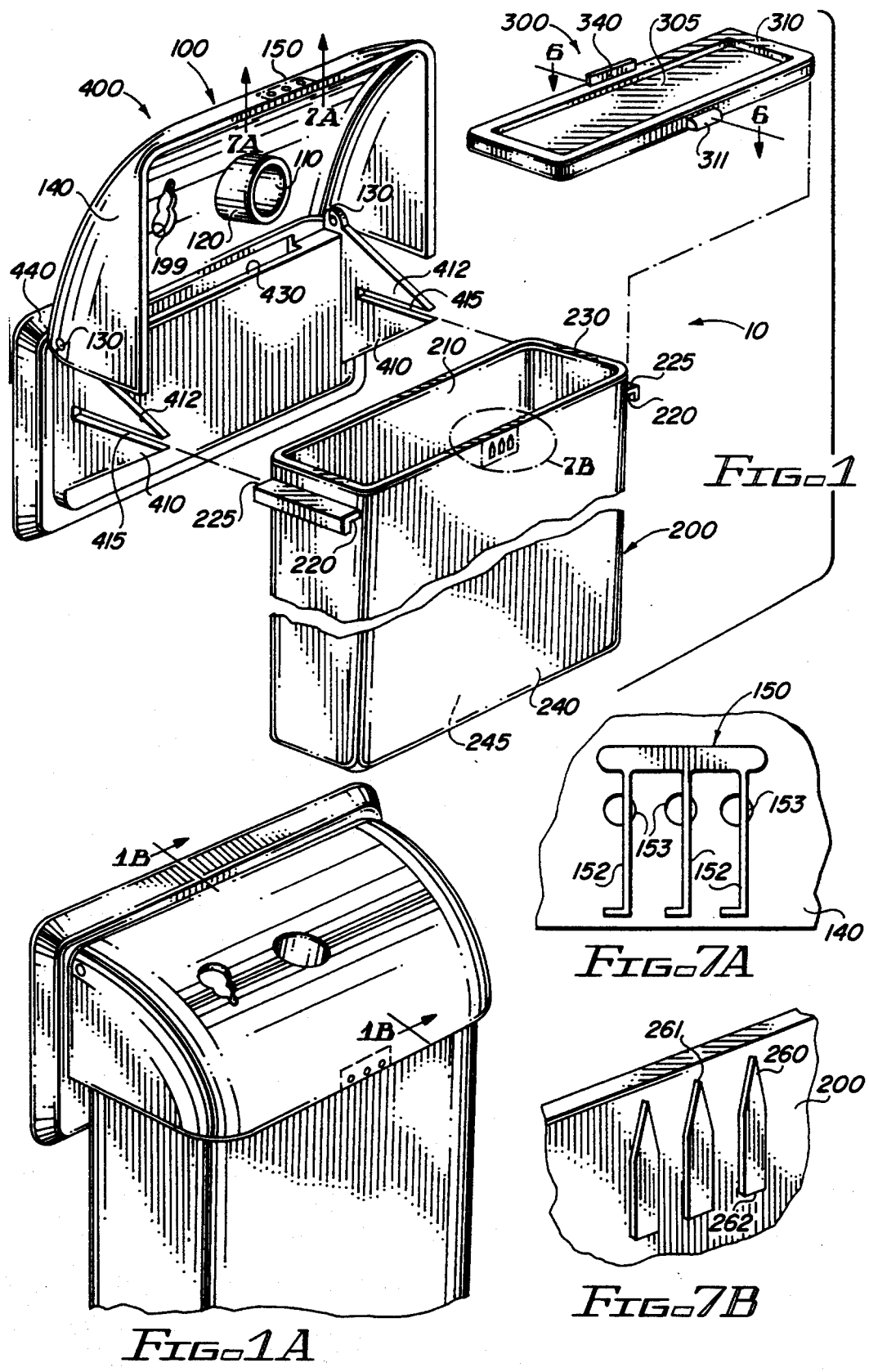

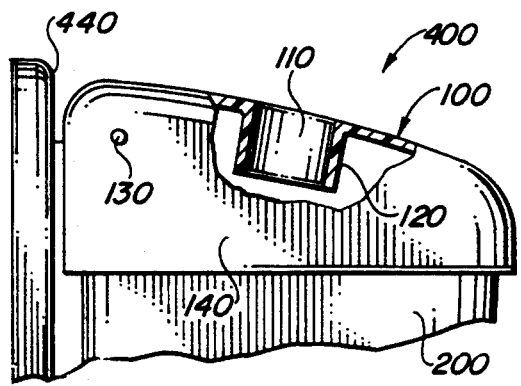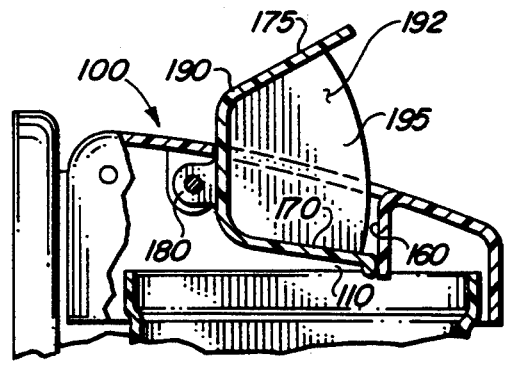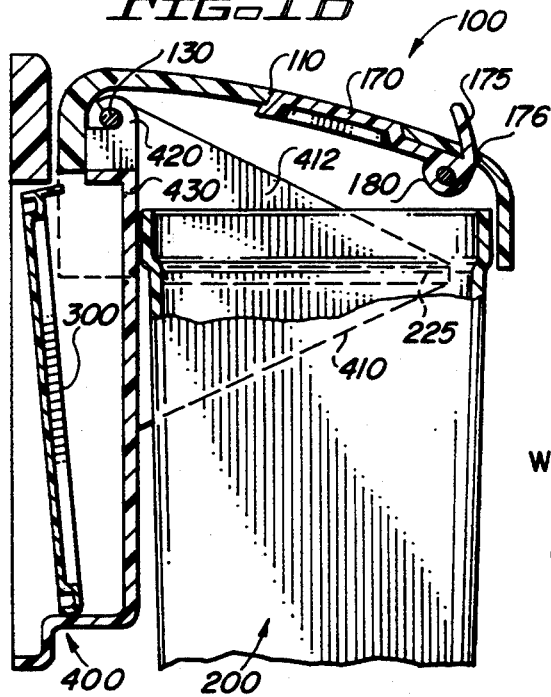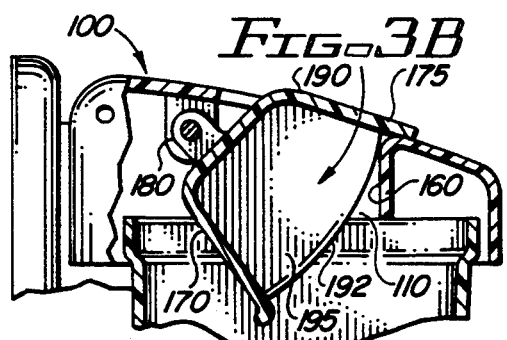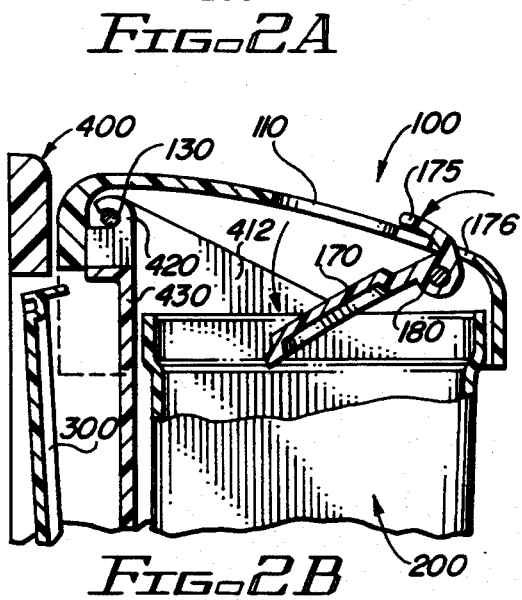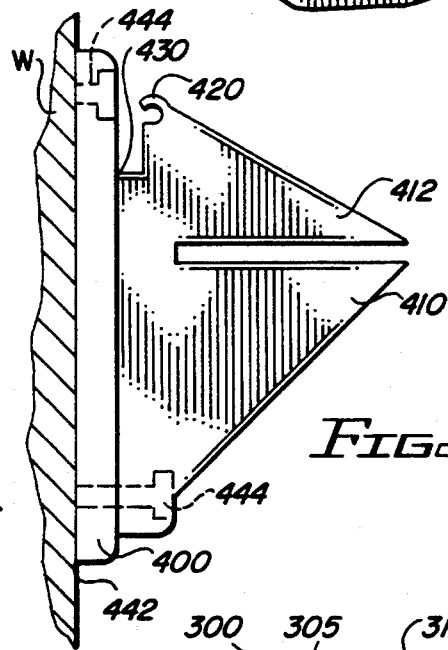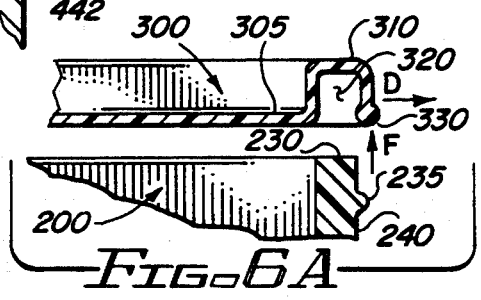

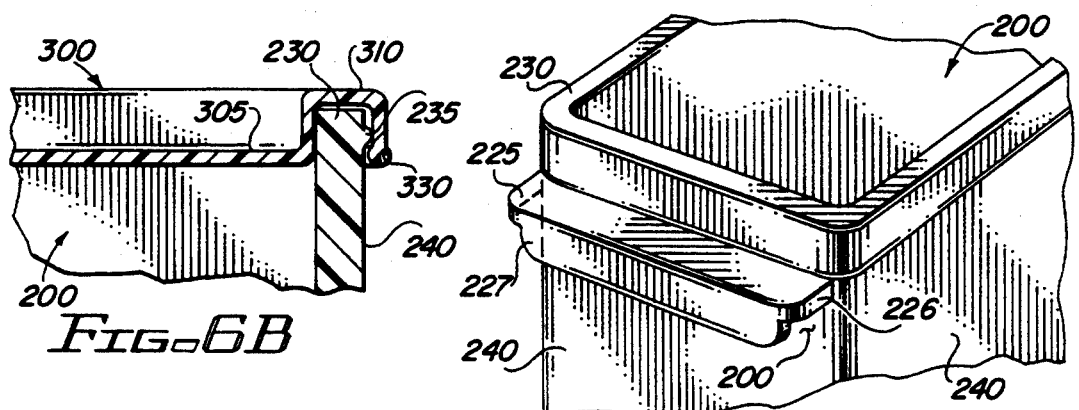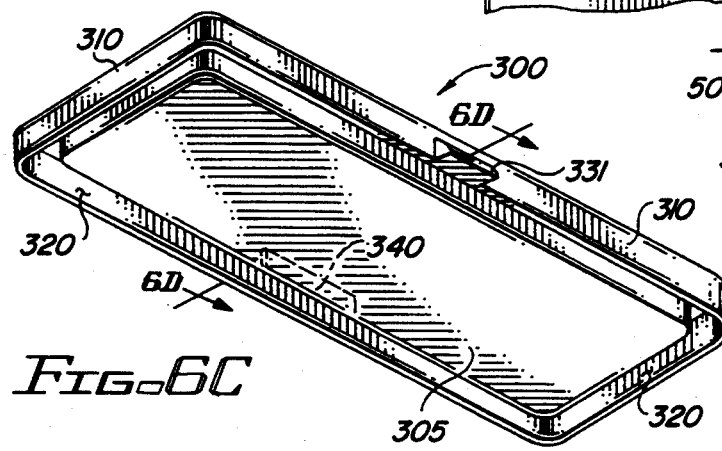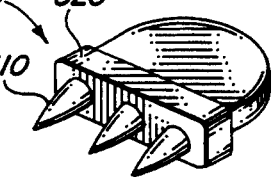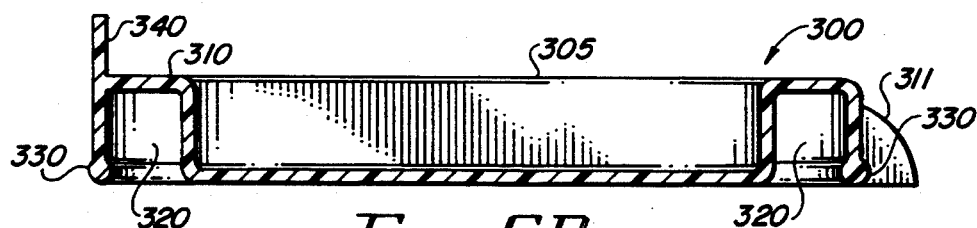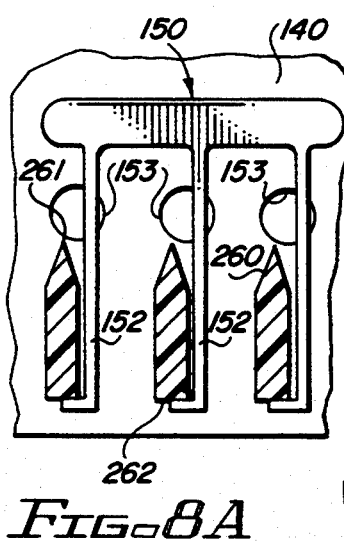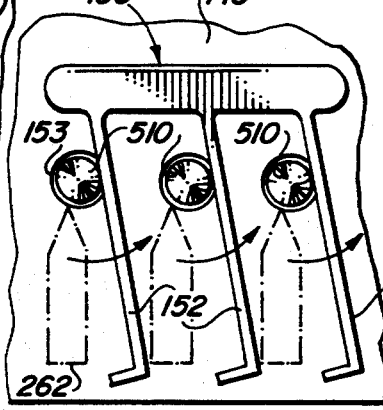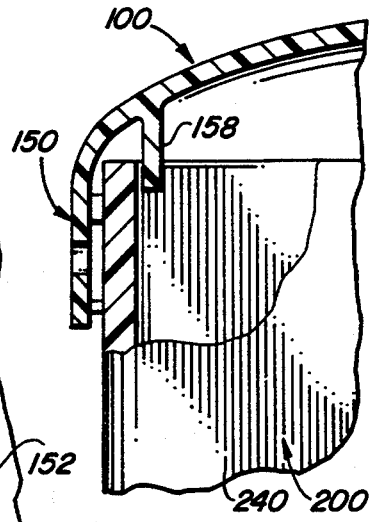

SHARPS DISPOSAL SYSTEM INCLUDING REUSABLE CONTAINER

TECHNICAL FIELD

The present invention relates to disposal systems for infectious hospital waste and sharps. More particularly, the present invention describes a secure disposal system designed to utilize a reusable container.

BACKGROUND OF THE INVENTION

Hospitals and the health care industry in general use great quantities of disposable implements such as needles, syringes, blades, and the like, commonly referred to as "sharps." Once used, these items present a disposal problem. The used sharps may not only be contaminated from use, but they present the added danger of potential puncture wounds. The sharps must be disposed so that they cannot be accessed without authorization or reused accidentally.

Many systems have been developed for the purpose of providing for safe disposal of sharps. Examples of such systems are generally illustrated in U.S. Pat. No. 4,453,648 to to Harris et al., U.S. Pat. No. 4,702,385 to Shillington et al., U.S. Pat. No. 4,715,498 to Hanifl, U.S. Pat. No. 4,736,860 to Bemis, U.S. Pat. No. 4,809,850 to Laible et al., U.S. Pat. No. 4,955,477 to Bruno, U.S. Pat. No. 5,046,613 to Baudry et al., U.S. Pat. No. 5,076,429 to Patrick et al., U.S. Pat. No. 5,103,997 to Shillington et al., and U.S. Pat. No. 5,277,312 to Vumbaca, all of which are incorporated herein by reference. These systems typically provide a container in which the sharps are disposed. They utilize various mechanisms to allow insertion of sharps and prevent access to the sharps inside the container ("insertion mechanism"). Most of these systems employ disposable containers, in which the insertion mechanism can be permanently locked, sealing the contents inside.

These systems have a disadvantage which would not be obvious to an artisan considering the issue of sharps disposal. The problem is the increased waste and expense involved in the use of disposable containers. This problem is compounded by the fact that the mechanism for locking the contents inside and the insertion mechanism are generally integral with or permanently affixed to the container, and, therefore, both must generally be dispensed with the container.

These problems can be solved by providing a system which employs a reusable container. In addition, even a reusable container could be expensive and burdensome to use. This is because either the container must be emptied, decontaminated and returned to service almost immediately upon filling to capacity, or more than one container must be rotated into use. It is difficult to imagine being able to treat and return a container to service quickly enough to obviate the need for several containers, especially considering the rate at which hospitals use sharps and the economies that can be affected by employing off-site treatment facilities. If more containers must be employed, then their cost-per-unit should be kept to a minimum. This can be accomplished by providing a system which employs simple, reusable containers and a separate, insertion mechanism which remains affixed on-site. Thus, the insertion mechanism remains in use, with a new container, when a full container is removed for treatment. For each system, only one insertion mechanism need be purchased.

Accordingly, there is a need for an improved sharps disposal system which utilizes a reusable container, while providing the necessary safety features to avoid accidental punctures or contact with potentially hazardous contaminants. There is an additional need for such an improved sharps disposal system to include a permanent insertion mechanism, allowing for an efficient, cost-effective, and safe method of exchanging sharps disposal containers.

SUMMARY OF THE INVENTION

The invention overcomes the difficulties encountered in the prior art by providing a satisfactory device for safely disposing of used sharps in an efficient, cost-effective, reusable manner.

Broadly stated, the present invention provides a sharps disposal system. The present invention provides a simple and efficient system employing a configuration which allows the sharps container to be reused, obviating the need for and expense associated with disposable containers.

More particularly, the invention provides a frame, a container having an opening, a means for removably mounting the container to the frame, a lid pivotally attached to the frame, wherein the lid selectively engages the container to cover the opening of the container and to impede removal of the container from the frame when the container is mounted to the frame, the lid having an aperture which allows insertion of sharps into the container and impedes insertion of human hands, and a means for selectively locking the lid into engagement with the container.

An alternative embodiment of the present invention provides a cover for selectively sealing the opening of the container. Also, in an alternative embodiment of the present invention, the frame is mountable to a vertical structure. The means for selectively mounting the container to the frame may include a bracket extending from the frame and a receptor positioned on the container selectively engaging the bracket.

In an alternative embodiment of the present invention, the container includes a substantially rectangular bottom and a plurality of substantially vertical walls extending upward from the perimeter of the bottom, the walls terminating in a rectangular rim defining the opening. Additionally, the bracket includes a parallel pair of cantilevers, and the receptor is an appendage extending from the container defining a bearing surface which corresponds to the cantilevers. Further, the appendage may be a pair of elongated handles opposite one another on the container. The lid may further include a rigid skirt extending therefrom such that the skirt covers the cantilevers and the handles when the lid engages the container. The means for selectively locking the lid into engagement may be a lock disposed in the skirt for engaging one of the walls of the container.

An alternative embodiment of the present invention provides a sleeve extending through the aperture for defining a passage into the container. Alternatively, the present invention may provide a mechanism for selectively closing the aperture of the lid. The mechanism for selectively closing the aperture may include a gate pivotally mounted to the lid, a lever extending from the gate, and a spring biasing the gate against the lid such that the gate closes the aperture, whereby the lever, when depressed, swings the gate away from the lid to open the aperture.

In an alternative embodiment of the present invention, the cover is detachable, and the frame has a pocket for selectively storing the cover. Further, the cover may include a rectangular planar surface corresponding in shape and size to the opening and an elastically deformable lip defining the perimeter of the planar surface for fitting snugly over the rim of the container. Additionally, the lip may be U-shaped having a groove for receiving and gripping the rim of the container.

In an alternative embodiment of the present invention, the lid is selectively releasable from the frame when the lid is not engaging the container. Alternatively, the lid is sloped away from the frame when the lid engages the container. Additionally, the lid may be translucent.

An alternative embodiment of the present invention provides sharps disposal system for use with an open container. More specifically, this alternative embodiment of the present invention provides a frame, a means for removably mounting the container to the frame, a lid pivotally attached to the frame, wherein the lid selectively engages the container to cover the opening of the container and to impede removal of the container from the frame when the container is mounted to the frame, the lid having an aperture which allows insertion of sharps into the container and impedes insertion of human hands, and a means for selectively locking the lid into engagement with the container. Alternatively, the present invention provides a cover for selectively sealing the container.

In an alternative embodiment of the present invention, the means for selectively locking includes a series of ribs on the container substantially near the rim, a corresponding series of elastically deformable hooks affixed to the inside of the skirt such that the hooks slide past and catch behind the ribs when the lid engages the container to prevent the lid from being disengaged from the container, and a means for releasing the hooks from behind the ribs to allow the lid to be disengaged from the container. The means for releasing may include a key having a series of tapered pins for selective insertion through a series pinholes in the skirt and corresponding to the series of hooks, wherein the pins, when inserted through the pinholes, force the hooks away from the ribs. A projection may extend from the lid for abutting the container in order to cooperate with the skirt to impede lateral separation of the lid from the container when said the is engaged to the container.

An alternative embodiment of the present invention provides a locking system for locking a lid into engagement with a container, including a series of ribs on the container, a corresponding series of elastically deformable hooks affixed to the inside of the lid such that the hooks slide past and catch behind the ribs when the lid engages the container to prevent the lid from being disengaged from the container, and a means for releasing the hooks from behind the ribs to allow the lid to be disengaged from the container. The means for releasing may be a key having a series of tapered pins for selective insertion through a series pinholes in the lid and corresponding to the series of hooks, wherein the pins, when inserted through the pinholes, force the hooks away from the ribs. A projection may extend from the lid for abutting the container to impede lateral separation of the lid from the container when the lid is engaged to the container.

An alternative embodiment of the present invention provides a reusable container for use with a sharps disposal system, which has a parallel pair of cantilevers, having a substantially rectangular bottom, a plurality of substantially vertical walls extending upward from the perimeter of the bottom, the walls terminating in a rectangular rim defining an opening in the container, and a pair of handles extending substantially horizontally from the container opposite one another corresponding to and for resting on the cantilevers.

Accordingly, it is an object of the present invention to provide a safe, simple and inexpensive sharps disposal system.

It is a further object of the present invention to provide a sharps disposal system which can employ reusable containers.

It is a further object of the present invention to provide a sharps disposal system in which the mechanism which allows insertion of sharps but prevents insertion of hands is separate from the container.

It is a further object of the present invention to provide a system in which the access-limiting lid is mounted to the frame to which the container can be coupled.

It is a further object of the present invention to provide a system in which the access-limiting lid is not permanently affixed to the container.

It is a further object of the present invention that the sharps disposal system can employ reusable containers.

It is a further object of the present invention that the container itself is the only portion of the system which must be removed from service for treatment when the container is full.

It is a further object of the present invention that the remainder of the invention, besides the container, can remain in continuous service, reducing the expense of the system.

It a further object of the present invention that the container itself is free of mechanisms which would complicate the treatment process.

These and other objects, features, and advantages of the present invention man be more clearly understood and appreciated from a review of ensuing detailed description of the preferred embodiment and by reference to the accompanying drawings and claims.

BRIEF DESCRIPTION OF THE DRAWINGS

FIG. 1 is an exploded, perspective view of the preferred embodiment of the present invention.

FIG. 1A is a perspective view of the preferred embodiment of the present invention, with the lid in its closed position.

FIG. 1B is a cut-away cross-sectional side view of the preferred embodiment of the present invention, along line 1B—1B of FIG. 1A, illustrating the positioning of the aperture within the closed lid.

FIG. 2A is a cut-away side view of the preferred embodiment of the present invention employing a gated horizontal drop, with the gate in the closed position.

FIG. 2B is a cut-away side view of the preferred embodiment of the present invention employing a gated horizontal drop, with the gate in the opened position.

FIG. 3A is a cut-away side view of the lid of the preferred embodiment of the present invention, employing an alternate gated horizontal drop, the gate in its receiving position.

FIG. 3B is a cut-away side view of the lid of the preferred embodiment of the present invention, employing an alternate gated horizontal drop, the gate in its depositing position.

FIG. 4 is a side view of the frame of the preferred embodiment of the present invention.

FIG. 5 is a perspective view of the container of the preferred embodiment of the present invention.

FIG. 6A is a cut-away side view of the cover of the preferred embodiment of the present invention, prior to sealing of the cover over the container.

FIG. 6B s a cut-away side view of the cover of the preferred embodiment of the present invention, subsequent to sealing of the cover over the container.

FIG. 6C is a perspective view of the cover of the preferred embodiment of the present invention.

FIG. 6D is a cross-sectional view of the cover of the preferred embodiment of the present invention, along line 6D—6D of FIG. 6C.

FIG. 7A is an elevational view of the portion of the lock located on the lid of the preferred embodiment of the present invention, from the interior of the lid along line 7A—7A of FIG. 1.

FIG. 7B is a perspective view of the portion of the lock located on the exterior of the container of the preferred embodiment of the present invention, as referred to by reference point 7B of FIG. 1.

FIG. 7C is a perspective view of the key to be employed with the lock of the preferred embodiment of the present invention.

FIG. 8A is a partially sectional view of the lock of the preferred embodiment of the present invention, in the locked position.

FIG. 8B is a plan view of the lock of the preferred embodiment of the present invention, with the key inserted so that the lock is in the unlocked position.

FIG. 9 is a cut-away side view of the preferred embodiment of the present invention, illustrating the lid locked to the container.

DETAILED DESCRIPTION OF THE PREFERRED EMBODIMENT

Referring now to the drawings, in which like numerals indicate like elements throughout the several views, FIG. 1 shows a preferred embodiment of a sharps disposal system 10 comprising a container 200, a frame 400, a lid 100, and a cover 300. In FIG. 1, the system 10 is exploded to better display the various parts. The container 200 includes an opening 210 for receiving disposed sharps. During use, the container 200 is mounted to the frame 400. The lid 100, which is pivotally mounted to the frame 400, closes over the opening 210 of the container 200. A lock 150, more clearly illustrated in FIG. 7-9, on the lid 100 can be locked to ensure that the lid 100 cannot be opened by an unauthorized person. An aperture 110 is provided through the lid 100 to allow insertion of the sharps. The cover 300 is provided to close the opening 210 completely, sealing the contents inside a full container 200 prior to removal of the container 200 from the frame 400.

In the preferred embodiment, the container 200 is substantially rectangular in shape. The container 200 has a closed, rectangular bottom 245 and substantially vertical walls 240 extending upwardly from the bottom 245. The walls 240 terminate in an opening 210, defined by a rectangular rim 230 formed by the terminal ends of the walls 240. The rectangular shape of the container 200 facilitates the mounting of the container 200 to the frame 400, as discussed with respect to FIG. 4. The container 200 may be configured in different shapes, so long as it includes an opening 210.

The container 200 can be of any suitable material, be it ceramic, metal, or polymer. The material of the container 200 will be determined by several factors. First, the material must be sufficiently strong so that the sharps disposed therein will not puncture the container 200. Second, because it is desired that the container 200 be reused, the material must be such that it can withstand the treatment and decontamination process to which the container 200 will be subjected. Therefore, the treatment process will dictate to some extent what material may be used. In the preferred embodiment, the material is rigid plastic, which will withstand the most common treatment methods and can be produced inexpensively through injection molding.

The frame 400 is preferably secured at its base 440 to a fixed structure (not shown), such as a floor, wall ceiling, or door. The system 10 is more secure with the frame 400 affixed to such a structure, because the system 10 is less likely to be removed in its entirety by an unauthorized person. It is preferred that the frame 400 be mounted to a wall, because its vertical disposition is the most space efficient, and a wall is more secure than a door. If desired, the frame 400 may alternatively be secured to a cart.

The system 10 includes a mechanism for selectively coupling the container 200 to the frame 400. The preferred embodiment shows a parallel pair of cantilever arms 410 extending from the frame 400. Above each of the cantilever arms 410 is a guide arm 412. The cantilever arms 410 and guide arms 412 form a pair of guide channels 415 therebetween. The container 200 is provided with matching bearing surfaces 220 on opposing walls 240 of the container 200 for engaging the cantilevers 410. The bearing surfaces 220 are formed by appendages 225 extending from the container 200. The appendages 225 slide into the guide channels 415 so that the bearing surfaces 220 rest on the cantilevers 410. The bearing surfaces 220 may be separate from one another or may be continuous, extending around the container 200, as long as there is a bearing surface 220 at each point of interface with a cantilever 410. The appendages 225 forming the bearing surfaces 220 can serve alternatively as handles during transport of the container 200. Placing the bearing surfaces 220 on top of the cantilevers 410 allows the container 200 to rest on the cantilevers 410 and to be supported thereby.

The coupling mechanism can be varied. For instance, the guide arm 412 need not be provided. If this is the case, then the bearing surfaces 220 need not be formed by appendages 225. The bearing surfaces 220 may alternatively be defined by bearing channels (not illustrated), disposed directly in the walls 240 of the container 200 and into which the cantilevers 410 can slide. Additionally, the cantilevers 410 need not be parallel if the container 200 is not rectangular, nor is it vital that they be paired. The cantilevers 410 may be substantially horizontal, as shown, or may incline either toward or away from the frame 400. If the cantilevers 410 do incline away from the frame 400, a means must be provided for keeping the container 200 from sliding off the frame 400. Alternatively, the cantilevers 410 may be shaped differently. In the preferred embodiment, the cantilevers 410 are thickest adjacent the frame 400 and narrow as they extend outward. This is done to provide better weight support. The cantilevers 410 may alternatively be substantially consistent in thickness throughout their length. The coupling can be accomplished by a means not employing cantilevers 410 at all, for example by a simple hook-and loop combination (not illustrated).

The lid 100 is designed to fit over the container 200. Therefore, the shape of the container 200 will dictate the shape of the lid 100. In the preferred embodiment shown in FIG. 1, the lid 100 is substantially rectangular in shape so as to conform with the shape of the container 200. The lid 100 can pivot on the frame 400 around the axis of rotation defined by pivot pins 130, so that, in the preferred embodiment, the lid 100 swings up and down between open and closed positions. When the container 200 is coupled to the frame 400, the lid 100 swings down until it engages the container 200 and covers the opening 210, as shown in FIG. 1A-1B.

With the lid 100 in its open position, slot 430 in the frame 400 can be accessed. This slot 430 is for storing the cover 300 when not in use. Keeping the cover 300 in this slot 430 prevents it from being accessed without lifting the lid 100, which protects against tampering or removal of the cover 300.

In the preferred embodiment, a skirt 140 descends from the lid 100. The skirt 140 is designed to cover the coupling mechanism when the lid 100 is closed over the container 200. This adds security against tampering. The lid 100 preferably does not have a skirt 140 descending from the edge which is pivotally attached to the frame 400.

A lock 150 is provided to prevent unauthorized access to the contents of the system 10. The lock 150 secures the lid 100 so that it remains closed over the container 200, and holds the container 200 in place. In the preferred embodiment, the lock 150 is disposed in the skirt 140 of the lid 100 opposite its connection to the frame 400. This allows the lid 100 to be locked directly to the container 200 and keeps the container 200 from being removed from the frame 400. The lock 150 is not shown in detail because any suitable lock well known in the field can be utilized. It is desirable that the lock 150 not require any apparatus on the container 200 itself which might be corroded during treatment of the container 200. One example of a means to accomplish this is to provide the container 200 with a simple depression for receiving a locking pin when the lock is engaged. The entire locking mechanism could be housed in the lid 100 itself, except for the depression in the container 200.

The lid 100 may be provided with a mechanism for selectively removing the needles from syringes prior to disposal of the syringes in the container 200. This mechanism may be any of a number of means, for example a stepped-teardrop notch 199 as shown in FIG. 1. The syringe is inserted, needle-first, into the notch 199. The syringe is then slid as far as possible toward the narrow portion of the notch 199. The syringe is then twisted, causing the needle to unscrew from the syringe and allowing the needle to drop into the container 200.

An aperture 110 passes through the lid 100. The aperture 110 is designed to allow insertion of sharps but to impede the insertion of a hand. FIG. 1 shows one variation of the aperture 110. In this embodiment, the aperture 110 is designed so that sharps are inserted vertically. The aperture 110 is large enough to accommodate vertically disposed sharps but too narrow for a hand. A sleeve 120, extending into the container 200, surrounds the aperture 110 to define a passage into the container 200 in order to direct sharps into the container 200 and protect against the insertion of hands or fingers into the container 200 where they might contact the sharps.

FIG. 2A-2B show the lid 100 in its closed position over the container 200 with an alternate design for the aperture 110. In this embodiment, the aperture 110 is elongated and narrow to receive horizontally disposed sharps. Additionally, the lid 100 is provided with a mechanism for selectively covering the aperture 110 when not in use. This is done with a gate 170 pivotally mounted to the lid 100 so that it can swing to close the aperture 110. A spring 180 biases the gate 170 against the lid 100 so that it closes the aperture 110. A lever 175 extends from the gate 170. Depressing the lever 175 moves the gate 170 away from the lid 100 and opens the aperture 110.

In this embodiment, the gate 170 is pivotally mounted to the inside of the lid 100. The spring 180 biases the gate 170 upward against the lid 100 closing the aperture 110. The lever 175 extends up from the gate 170 substantially adjacent to its pivotal connection to the lid 100 and forms an acute angle with the gate 170. The lever 175 passes through a small hole 176 in the lid 100 so that it is located primarily outside the lid 100. Pushing the lever 175 toward the lid 100 forces the gate 170 to swing down and away from the lid 100, opening the aperture 110. With this configuration, while holding a sharp in the fingers of one hand, a user can depress the lever 175 with the heel of that hand, opening the aperture 110 to deposit the sharp in the container 200. This one-handed configuration minimizes the chance that the user will accidentally injure himself or herself when disposing of sharps.

FIG. 2 also provides a cutaway view showing the cover 300 stored in the slot 430 in the frame 400 behind the container 200. FIG. 2 also illustrates another optional feature of the invention. The lid 100 may be sloped away from the frame 400 to prevent objects from being rested thereon. This reduces the danger that a used syringe or other dangerous object will be placed on the lid 100 and forgotten, where it might later cause an injury. Additionally, the lid 100 may be translucent so that the contents of the container 200 can be observed without opening the lid 100. If this done, the container 200 can be provided with a fill-line (not shown) on its inner wall to indicate when it is full and should be removed for treatment.

FIG. 2 shows pivot sockets 420 extending from the base 440 just above the cantilevers 410 and guide arms 412 (not shown in FIG. 2). The pivot sockets 420 are provided to receive and form a pivotal connection with the pivot pins 130 of the lid 100. This allows the lid 100 to pivot about the axis (perpendicular to the plane of FIG. 2) established by the pivot sockets 420. When the pivot pins 130 are nested in the pivot sockets 420, the sockets 420 allow the pivot pins 130 to rotate therein. The pivot sockets 420 are C-shaped to provide a mechanism for removing the lid 100 from the frame 100. The sockets 420 allow the pins 130 to slide horizontally toward the base 440. If the lid 100 is not impeded by the container 200, it can be removed by sliding it toward the base 440 until the pins 130 slide out of the sockets 420. The lid 100 is designed to fit snugly over the container 200 so that, whenever the lid 100 is down in its closed position, the container 200 impedes the lid 100 from sliding toward the base 440 and being disengaged from the frame 400. In the preferred embodiment, the lid 100 is designed to fit over the sockets 420 so that the pins 130 extend inward from the lid 100 to engage the sockets 420. This provides added security in that the connection is not exposed when the system 10 is locked closed.

The mechanism for selectively covering the aperture 110 may be designed in other ways. For instance, the gate 170 could be positioned on the outside of the lid 100, and the lever 175 could extend from the gate 170 at an obtuse angle, with the gate 170 biased downward against the lid 100. In this alternate configuration, depressing the lever 175 with one hand would lift the gate 170 so that sharps could be deposited through the aperture 110 with the other hand. The raised gate 170 would effectively shield the hand depressing the lever 175 from the sharps being deposited.

FIG. 3 shows the preferred embodiment of the horizontal drop lid 100 with the selective closure mechanism. In FIG. 3A, the gate 170 and the lever 175 are each elongated and substantially arcuate. They combine to form the partially cylindrical door 190 with an open face 192 and closed ends 195. The cradle-shaped door 190 is nested in and substantially fills the aperture 110. The door 190 is pivotally connected to the lid 100 so that it swings freely within the aperture 110 between a receiving position, illustrated in FIG. 3A, and a depositing position, illustrated in FIG. 3B. The spring 180 biases the door 190 into its receiving position, in which the gate 170 is pressed against the inside of the lid 100 closing the aperture 110. When the door 190 is in its receiving position, sharps can be inserted into the "cradle" onto the gate 170. Exerting a downward force, strong enough to overcome the force of the spring 180, on the door 190 will move it into its depositing position shown in FIG. 3B in which the lever 175 presses against the lid 100 to close the aperture 110. The angle between the gate 170 and the lever 175 is acute but open enough so that, when the door 190 is in its depositing position, the gate 170 will be sloped away from the pivotal connection, allowing the sharps to roll off of the gate 170 into the container 200.

The only time the aperture 110 is open is when the door 190 is between its receiving and depositing positions, and then it can only be penetrated via the circuitous route through the cradle of the door 190. To enhance safety, in its preferred embodiment the lid 100 has a guard 160 descending from the aperture 110 opposite the side of the aperture 110 nearest the pivotal connection of the door 190 to the lid 100. This guard 160 extends substantially the entire width of the aperture 110 and descends from the lid 100 a distance that is sufficient to impede insertion of fingers when the door 190 is between its insertion and depositing positions, but does not impede sharps from rolling off the gate 170 when the door 190 is in its down position.

In the preferred embodiment, the spring 180, which is shown as a coil-type spring but may be any suitable form, is calibrated so that it barely overcomes the weight of the door 190 to bias the door 190 into its receiving position. Thus, the added weight provided by merely inserting a sharps into the cradle of the door 190 will cause the door 190 to swing into its depositing position. The sharps will then roll off the door 190, and the spring 180 will then slowly return the door 190 to its receiving position. If the weight of the sharps is not sufficient to swing the door 190, a light, downward tap only need be exerted on the outside of lever 175 to swing the door 190 and deposit the sharps in the container 200.

FIG. 4 illustrates the preferred embodiment of the frame 400 in isolation. The base 440 is substantially hollow with an open back. The back of the base 440 touches the wall ("W") around its substantially rectangular perimeter 442. The slot 430 in the base 440 allows storage of the cover 300 (not shown in FIG. 4) in the space between the hollow base 440 and the wall W. The base 440 is affixed to the wall by conventional means depending upon the construction of the wall, for example by using drywall anchors or the like. The means for affixing the base 440 to the wall W must be disposed on the base 440 so as not to interfere with the storage of the cover 300 behind the base 440. In the preferred embodiment, the base 440 is provided with anchor holes 444, through which anchoring bolts or the like can be inserted, substantially near its corners. Pivot sockets 420 extend from the base 440 just above the cantilevers 410 and guide arms 412. As can be seen from FIG. 4, the sockets 420 are substantially integral with the cantilevers 410. Therefore, with the lid 100 (not shown) pivotally mounted to the outside of the sockets 420, the lid 100 will close snugly over the cantilevers 410.

FIG. 5 shows the preferred container 200 in isolation. The opening 210 of the container 200 is substantially rectangular, as defined by the rim 230 which is in turn formed by the terminal ends of the walls 240. The handles 225 extend outward from two opposing walls 240. The handles 225 are elongated and run substantially the entire length of the walls 240 from which they extend. The handles 225 extend from the walls 240 substantially near the rim 230. From this view, the handles 225 are shown to be L-shaped, forming a bearing surface 200 below the handles 225 for receiving the cantilevers 410 (not shown in FIG. 5). The horizontal portions 226 of the handles 225 extend substantially the entire length of the walls 240 from which they extend, while the vertical portions 227 are somewhat shorter. The walls 240 are substantially vertical, extending upward from a closed bottom 245 and terminating at the rim 230.

FIG. 6A shows a detail of the walls 240 near the rim 230 in one embodiment of the present invention. In this embodiment, a small bump 235 is disposed on the wall 240 near the rim 230. This is provided for interaction with an embodiment of the cover 300, and the significance of the bump 235 will be made apparent later.

FIG. 6 illustrates the cover 300 itself, which is provided for sealing the container 200 prior to removal of the container 200 from the frame 400. The cover 300 is designed to fit over the opening 210 and render the container 200 leak-proof. In one embodiment, as shown in FIG. 6A, the cover 300 is comprised of a planar surface 305 which has the same shape as the opening 210 (the features of the container 200 are not shown in FIG. 6). A U-shaped lip 310 forms the perimeter of the planar surface 305. The lip 310 defines a groove 320, seen in FIG. 6C and FIG. 6D. The groove 320 corresponds in shape to the rim 230 of the container 200. In the preferred embodiment, the groove 320 is elastically deformable, and must deform slightly to accept the rim 230. Therefore, the elastic nature of the groove 320 will cause the groove 320 to squeeze the rim 230, forming a tight seal. As can be seen in the detailed view of the lip 310 in FIG. 6D, the lip 310 can be provided with a bulge 330 at the mouth of the groove 320 so that the groove 320 is slightly wider at its base than at its mouth. In this embodiment, the bulge 330 is rounded in shape so that a substantially vertical, off-center force applied to the bulge 330, as illustrated in FIG. 6A by arrow F, will cause the bulge 330 to be deflected horizontally, as shown by arrow D of FIG. 6A. Therefore, as the cover 300 is placed on the container 200, the bulge 330 will encounter the bump 235 (discussed with reference to FIG. 5(d)) which is disposed on the wall 240 near the rim 230. Applying additional force will deflect the bulge 330, allowing the bump 235 to slide by the bulge 330, and snapping the cover 300 into place with the bump 235 in the groove 320 behind the bulge 330. When the rim 230 is fully inserted into the groove 320, the bulge 330 will hold the bump 235 behind it and will act to keep the cover 300 on the container 200.

The bump 235 and the bulge 330 may be on either side of the wall 240 and groove 320 respectively, so long as they are positioned to interact with one another when the cover 300 is placed on the container 200. The bump 235 and the bulge 330 can be shaped to allow easy insertion of the rim 230 into the groove 320 in order to secure the cover 300 to the container 200, while making it difficult to remove the cover 300 once snapped into place. By providing less severe angles on the sides of the bump 235 and bulge 330 where they engage one another during insertion, the insertion can be made easier. By making the angles more severe on the opposite sides, the removal can be made more difficult. The cover 300 and container 200 may even be configured so that the cover 300 cannot be removed without mechanical aid, so that the full containers 200 can be stored at the hospital prior to treatment with less concern for tampering. The cover 300 may be provided with a removal tab 340 disposed on or near the lip 340 to facilitate removal of the cover 300 with mechanical aid at the treatment facility. This removal tab 340 can be configured in any of a number of ways to provide the mechanical advantage needed to unsnap the cover 300.

In an alternative embodiment, the lip 310 is not U-shaped, and therefore has no groove 320. The lip 310 simply descends perpendicularly from the perimeter of the planar surface 305. Instead of accepting the rim 230 into a groove 320, as in the previously discussed embodiment, the lip 310 snugly fits over the outside of the rim 230, forming a seal. Pressing down briefly on the planar surface 305, when the cover 300 is in place on the container 200, forces air out between the lip 310 and the rim 230, creating a partial vacuum which holds the cover 300 in place. Depending on the placement of the locking mechanism 150 on the container 200, the cover 300 may have to be shaped to accommodate it. For example, the lip 310 may have to be provides with a hood 311 to fit over the raised ribs (not shown) in the container 200, discussed below. In this embodiment, because there is no groove or bulge in the cover 300, there is not a bump disposed on the container 200 near the rim 230.

FIG. 7-8 illustrate a preferred embodiment of the lock 150 on a simplified embodiment of the lid 100 in which the aperture 110 is a simple hole. As seen in FIG. 7A, a series of elastically-deformable, barbed teeth 152 are disposed on the inside of the skirt 140. The teeth 152 are disposed over a matching series of small pinholes 153 in the skirt 140. FIG. 7B shows the matching raised ribs 260 on the container 200. The ribs 260 are tapered so that as the lid 100 is closed on the container 200 the teeth 152 will be deflected as they first contact the leading edges 261 of the ribs 260. The ribs 260 have a flat trailing edges 262 so that the teeth 152 will catch behind the ribs 260 when the lid 100 is fully closed. Therefore, when the lid 100 is closed over the container 200, it will automatically lock into place. With the barbed teeth 152 caught behind the ribs 260, as illustrated schematically in FIG. 8A, the lid 100 cannot be opened unless the teeth 152 are deflected so that they can clear the trailing edges 262 of the ribs 260. This is accomplished with the key 500, illustrated in FIG. 7C. The key 500 has a grip 520, and series of conical pins 510 which match the pinholes 153 in the skirt 140. When the pins 510 are fed through the pinholes 153, the pins 510 contact the teeth 152 and deflect them away from the ribs 260. With the key 150 fully inserted in the pinholes 153, the teeth 152 will be deflected sufficiently to allow the lid 100 to be opened, as illustrated in FIG. 8B.

The security provided by the lock 150 is improved if the lid 100 is provided with a projection 158 as shown in FIG. 9. The lock 150 is not illustrated in detail in FIG. 9 because any of the locking means discussed herein may benefit from the feature shown here. The projection 158 slides inside the wall 240 of the container 200 opposite the lock 150 when the lid 100 is closed over the container 200. The projection 158 and the skirt 140 are spaced apart so that the wall 240 of the container 200 and the lock 150 fit snugly therebetween. This snug fit inhibits lateral movement of the lid 100 relative to the container 200 when the lid 100 is closed over the container 200. This is designed to prevent the lid 100 from being separated from the wall 240 of the container 200 far enough to disengage the lock 150, which would allow the lid 100 to be opened while still "locked."

The operation of the system 10 is quite simple and efficient. An empty container 200 is loaded on the frame 400 by placing the bearing surfaces 220 on top of the cantilevers 410. The lid 100 is then closed over the opening 210 in the container 200 as well as the cantilevers 410 and locked into place. Sharps are deposited in the container 200 through the aperture 110. Once the container 200 is full, the lid 100 is unlocked and opened. With the lid 100 open, the cover 300 can be removed from the slot 430. The cover 300 is placed on the container 200, sealing the contents inside. The full container 200 can then be removed from the frame 400 and replaced with any empty one. The full container 200 can then be safely stored or transported for treatment.

Accordingly, it will be understood that both the preferred and alternative embodiments of the present invention have been disclosed by way of example and that other modifications and alterations may occur to those skilled in the art without departing from the scope and spirit of the appended claims.

What is claimed is:

1. A sharps disposal system comprising:
    a frame;
    a container having an opening;
    means for removably mounting said container to said frame;
    a lid pivotally attached to said frame, wherein said lid selectively engages said container to cover said opening of said container and to impede removal of said container from said frame when said container is mounted to said frame; said lid having an aperture which allows insertion of sharps into said container and impedes insertion of human hands; and
    means for selectively locking said lid into engagement with said container.

2. The sharps disposal system of claim 1 further comprising a cover for selectively sealing said opening of said container.

3. The sharps disposal system of claim 2 wherein said frame is mountable to a vertical structure.

4. The sharps disposal system of claim 3 wherein said means for selectively mounting said container to said frame comprises:
   a bracket extending from said frame; and
   a receptor positioned on said container selectively engaging said bracket.

5. The sharps disposal system of claim 4 wherein said container comprises a substantially rectangular bottom and a plurality of substantially vertical walls extending upward from the perimeter of said bottom, said walls terminating in a rectangular rim defining said opening.

6. The sharps disposal system of claim 5 wherein:
   said bracket comprises a parallel pair of cantilevers; and
   said receptor comprises an appendage extending from said container defining a bearing surface which corresponds to said cantilevers.

7. The sharps disposal system of claim 6 wherein said appendage comprises a pair of elongated handles opposite one another on said container.

8. The sharps disposal system of claim 7 wherein said lid further comprises a rigid skirt extending therefrom such that said skirt covers said cantilevers and said handles when said lid engages said container.

9. The sharps disposal system of claim 8 wherein said means for selectively locking said lid into engagement comprises a lock disposed in said skirt for engaging one of said walls of said container.

10. The sharps disposal system of claim 1 further comprising a sleeve extending through said aperture for defining a passage into said container.

11. The sharps disposal system of claim 1 further comprising a mechanism for selectively closing said aperture of said lid.

12. The sharps disposal system of claim 11 wherein said mechanism for selectively closing said aperture comprises:
   a gate pivotally mounted to said lid;
   a lever extending from said gate; and
   a spring biasing said gate against said lid such that said gate closes said aperture;
   whereby said lever, when depressed, swings said gate away from said lid to open said aperture.

13. The sharps disposal system of claim 5 wherein:
   said cover is detachable; and
   said frame has a pocket for selectively storing said cover.

14. The sharps disposal system of claim 13 wherein said cover comprises:
   a rectangular planar surface corresponding in shape and size to said opening; and
   an elastically deformable lip defining the perimeter of said planar surface for fitting snugly over said rim of said container.

15. The sharps disposal system of claim 14 wherein said lip is U-shaped having a groove for receiving and gripping said rim of said container.

16. The sharps disposal system of claim 1 wherein said lid is selectively releasable from said frame when said lid is not engaging said container.

17. The sharps disposal system of claim 1 wherein said lid is sloped away from said frame when said lid engages said container.

18. The sharps disposal system of claim 1 wherein said lid is translucent.

19. A sharps disposal system for use with an open container comprising:
   a frame;
   means for removably mounting said container to said frame;
   a lid pivotally attached to said frame, wherein said lid selectively engages said container to cover said opening of said container and to impede removal of said container from said frame when said container is mounted to said frame; said lid having an aperture which allows insertion of sharps into said container and impedes insertion of human hands; and
   means for selectively locking said lid into engagement with said container.

20. The sharps disposal system of claim 19 further comprising a cover for selectively sealing said container.

21. The sharps disposal system of claim 8 wherein said means for selectively locking comprises:
   a series of ribs on said container substantially near said rim;
   a corresponding series of elastically deformable hooks affixed to the inside of said skirt such that said hooks slide past and catch behind said ribs when said lid engages said container to prevent said lid from being disengaged from said container; and means for releasing said hooks from behind said ribs to allow said lid to be disengaged from said container.

22. The sharps disposal system of claim 21 wherein said means for releasing comprises:
   a key comprising a series of tapered pins for selective insertion through a series of pinholes in said skirt corresponding to said series of hooks;
   wherein said pins, when inserted through said pinholes, force said hooks away from said ribs.

23. The sharps disposal system of claim 22 further comprising a projection extending from said lid for abutting said container in order to cooperate with said skirt to impede lateral separation of said lid from said container when said lid is engaged to said container.

24. A locking system for locking a lid into engagement with a container comprising:
   a series of ribs on said container;
   a corresponding series of elastically deformable hooks affixed to the inside of said lid such that said hooks slide past and catch behind said ribs when said lid engages said container to prevent said lid from being disengaged from said container; and
   means for releasing said hooks from behind said ribs to allow said lid to be disengaged from said container.

25. The locking system of claim 24 wherein said means for releasing comprises:
   a key comprising a series of tapered pins for selective insertion through a series of pinholes in said lid corresponding to said series of hooks;
   wherein said pins, when inserted through said pinholes, force said hooks away from said ribs.

26. The locking system of claim 25 further comprising a projection extending from said lid for abutting said container to impede lateral separation of said lid from said container when said lid is engaged to said container.

* * * * *